(12) United States Patent
Molla et al.

(10) Patent No.: US 10,569,267 B2
(45) Date of Patent: Feb. 25, 2020

(54) METHOD AND APPARATUS FOR CHARACTERIZING INORGANIC SCALE FORMATION CONDITIONS EMPLOYING A MICROFLUDIC DEVICE

(71) Applicant: SCHLUMBERGER TECHNOLOGY CORPORATION, Sugar Land, TX (US)

(72) Inventors: Shahnawaz Molla, Watertown, MA (US); Farshid Mostowfi, Lexington, MA (US); Cedric Floquet, Cambridge, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 15/503,305

(22) PCT Filed: Aug. 11, 2014

(86) PCT No.: PCT/US2014/050538
§ 371 (c)(1),
(2) Date: Feb. 10, 2017

(87) PCT Pub. No.: WO2016/024941
PCT Pub. Date: Feb. 18, 2016

(65) Prior Publication Data
US 2018/0221867 A1 Aug. 9, 2018

(51) Int. Cl.
*B01L 3/00* (2006.01)
*C09K 8/536* (2006.01)
(Continued)

(52) U.S. Cl.
CPC ............... *B01L 3/5027* (2013.01); *B01L 7/52* (2013.01); *C02F 5/08* (2013.01); *C09K 8/536* (2013.01);
(Continued)

(58) Field of Classification Search
None
See application file for complete search history.

(56) References Cited

U.S. PATENT DOCUMENTS 8,269,961 B2 9/2012 Mostowfi et al.
9,752,430 B2 9/2017 Mostowfi
(Continued)

FOREIGN PATENT DOCUMENTS

WO WO2013070283 A1 5/2013

OTHER PUBLICATIONS

Gallup, D. L., "Investigations of organic inhibitors for silica scale control in geothermal brines", Geothermics, 2002, 31(4), pp. 415-430.
(Continued)

*Primary Examiner* — Jeffrey D Washville (57) ABSTRACT

A test method and apparatus employs a microfluidic device to characterize properties of a fluid. The microfluidic device has an inlet port, an outlet port, and a microchannel as part of a fluid path between the inlet port and the outlet port. While a fluid is introduced into the microchannel, the fluid temperature is maintained while the fluid pressure in the microchannel is varied to characterize the properties of the fluid in the microchannel. The properties of the fluid can relate to a scale onset condition of the fluid at the pressure of the flow through the microchannel. In one aspect, fluid pressure in the microchannel is maintained while the fluid temperature is varied to characterize the properties of the fluid. In another aspect, flow rate of the fluid through the (Continued)

microchannel is varied while the fluid temperature is maintained to characterize the properties of the fluid in the microchannel.

5 Claims, 7 Drawing Sheets (51) Int. Cl.
　　*C09K 8/92*　　(2006.01)
　　*C02F 5/08*　　(2006.01)
　　*B01L 7/00*　　(2006.01)
　　*G01N 33/28*　　(2006.01)
(52) U.S. Cl.
　　CPC .......... *C09K 8/92* (2013.01); *B01L 2200/146* (2013.01); *B01L 2200/147* (2013.01); *B01L 2300/1822* (2013.01); *G01N 33/2835* (2013.01)

(56) References Cited

U.S. PATENT DOCUMENTS

| | | | |
|---|---|---|---|
| 2002/0166592 A1 | 11/2002 | Liu et al. | |
| 2009/0326827 A1 | 12/2009 | Mostowfi et al. | |
| 2010/0230613 A1 | 9/2010 | Pieprzyk et al. | |
| 2011/0253222 A1 | 10/2011 | Arai | |
| 2014/0238122 A1* | 8/2014 | Mostowfi | G01N 21/05 73/152.18 |

OTHER PUBLICATIONS

Gallup, D. L. et al., "Investigations of organic inhibitors for silica scale control from geothermal brines-II", Geothermics, 2005, 34(6), pp. 756-771.
Leng, J. et al., "Microfluidic crystallization" , Lab on a Chip—Miniaturisation for Chemistry and Biology, 2009, 9, pp. 24-34.
Puigmarti-Luis, J., "Microfluidic platforms: a mainstream technology for the preparation of crystals", Chemical Society Reviews, 2014, 43, pp. 2253-2271.
Chen, D .L. et al., "Using microfluidics to observe the effect of mixing on nucleation of protein crystals", Journal of the American Chemical Society, 2005, 127, 9672-9673.
Yashina, A. et al., "Calcium carbonate polymorph control using droplet-based microfluidics", Biomicrofluidics, 2012, 6(2), pp.
Sekine, K. et al., "In situ observation of the crystallization pressure induced by halite crystal growth in a microfluidic channel", American Mineralogist, 2011, 96(7), pp. 1012-1019.
Zhang, C. et al., "Pore-Scale Study of Transverse Mixing Induced CaCO3 Precipitation and Permeability Reduction in a Model Subsurface Sedimentary System", Environmental Science and Technology, 2010, 44(20), pp. 7833-7838.
Kim, M. et al.,"Aquifer-on-a-Chip: understanding pore-scale salt precipitation dynamics during CO 2 sequestration", Lab on a Chip—Miniaturisation for Chemistry and Biology, 2013, 13(13), pp. 2508-2518.

White, F. M. , "Poiseuille Flow through Ducts" in Viscous Fluid Flow, McGraw Hill New York, Third edn., 2005, ch. 3, pp. 107-117.
Al Nasser, W. N. et al., "Determining kinetics of calcium carbonate precipitation by inline technique", Chemical Engineering Science, 2008, 63(5), pp. 1381-1389.
Coto, B. et al., "Effects in the solubility of CaCO3: Experimental study and model description", Fluid Phase Equilibria, 2012, 324(25), pp. 1-20.
Dawe, R. A. et al., "Kinetics of calcium carbonate scaling using observations from glass micromodels", Journal of Petroleum Science and Engineering, 1997, 18(3-4), 179-187.
International Search Report and Written Opinion of International Patent Application No. PCT/US2014/050538, dated May 28, 2015, 17 pages.
International Preliminary Report on Patentability of International Patent Application No. PCT/US2014/050538, dated Feb. 23, 2017, 16 pages.
Yuan, M. D., E. Jamieson, et al. (1998). Investigation of Scaling and Inhibition Mechanisms and the Influencing Factors in Static and Dynamic Inhibition Tests. CORROSION 98. San Diego, California, NACE International (11 pages).
Graham, G. M., H. L. Williams, et al. (2005). Design and Application of a Novel HT/HP "Stirred Reactor" Test Rig to Study Scale Formation and Control. SPE International Symposium on Oilfield Chemistry. The Woodlands, Texas, Society of Petroleum Engineers (11 pages).
Graham, G. M., I. R. Collins, et al. (2002). The Importance of Appropriate Laboratory Procedures for the Determination of Scale Inhibitor Performance. International Symposium on Oilfield Scale. Aberdeen, United Kingdom, Society of Petroleum Engineers (14 pages).
Williams, H., R. M. S. Wat, et al. (2005). Scale Dissolver Application Under HP/HT Conditions—Use of a HP/HT "Stirred Reactor" for In-Situ Scale Dissolver Evaluations. SPE International Symposium on Oilfield Scale. Aberdeen, United Kingdom, Society of Petroleum Engineers (13 pages).
Graham, G. M., K. B. Melvin, et al. (2006). Simulating Calcium Naphthenate Formation and Mitigation Under Laboratory Conditions. SPE International Oilfield Scale Symposium. Aberdeen, UK, Society of Petroleum Engineers (11 pages).
Wyman, D. P., R. D. Moll, et al. (2002). A Convenient, Low Cost Laboratory Protocol for Screening Scale Inhibitors. CORROSION 2002. Denver, Colorado, NACE International (23 pages).
Guan, H. (2013). Selection of Scale Inhibitor for Geothermal Applications. CORROSION 2013. Orlando, Florida, NACE International (11 pages).
Chandler_Engineering_Dynamic_Scale_Deposition_Loop_System—https://www.chandlereng.com/products/viscosity-or-rheology/dynamic-scale-deposition-loop-system/model-5400 (4 pages).
NACE_standards_TM0197-97 (1997)—Laboratory Screening Test to Determine the Ability of Scale Inhibitors to Prevent the Precipitation of Barium Sulfate and/or Strontium Sulfate from Solution (for Oil and Gas Production Systems) (10 pages).
NACE standards TM 0374-2001 (2001)—Laboratory Screening Tests to Determine the Ability of Scale Inhibitors to Prevent the Precipitation of Calcium Sulfate and Calcium Carbonate from Solution (for Oil and Gas Production Systems) (7 pages).

* cited by examiner

METHOD AND APPARATUS FOR CHARACTERIZING INORGANIC SCALE FORMATION CONDITIONS EMPLOYING A MICROFLUDIC DEVICE

BACKGROUND

Field

The present application relates to the detection of the formation of inorganic scale and in particular, but not exclusively, to the measurement of pressures and corresponding temperatures at which inorganic scale is found to form.

Related Art

Inorganic scale (or scale) is a deposit or coating formed on the surface of metal, rock, or other material. Scale can be caused by precipitation due to a chemical reaction with the surface of such materials, by precipitation caused by chemical reactions in the fluid, by a change in pressure or temperature, and by a change in the composition of the fluid. Common scales are calcium carbonate, calcium sulfate, barium sulfate, strontium sulfate, iron sulfide, iron oxides, iron carbonate, the various silicates and phosphates and oxides, or any of a number of compounds insoluble or slightly soluble in water.

Scale formation is of interest in the petroleum industry, particularly with respect to producing, transporting, and processing of natural gas and petroleum fluids. In the case of oil and gas wells, scale may occur on wellbore tubulars and components as the saturation of produced water is affected by changing temperature and pressure conditions in the production conduit. In severe conditions, scale creates a significant restriction, or even a plug, in the wellbore tubulars. For example, damage due to inorganic scale formation in a well, formation, or reservoir during water injection at high pressure and high temperature (HPHT) conditions is a challenge to the petroleum industry. Scale removal is a common well intervention operation, with a wide range of mechanical, chemical, and scale inhibitor treatment options available. However, remediation and cleaning of water scales costs the petroleum industry millions of dollars each year.

At present, no standard laboratory test is available to accurately detect and measure the scale onset condition at reservoir conditions (which is often at high pressure and high temperature). Although, the thermodynamic models for scale prediction are well known and reliable, these models require very accurate composition of the water samples at reservoir conditions as primary input. However, acquiring a representative sample of the formation water to measure composition with a high degree of accuracy is a significant challenge; specifically when the sample must be transported to the laboratory in a pressurized container. Quite often the sample integrity is compromised due to changes in pressure and temperature as well as compositional variation during transportation. Hence, it is important to measure the scale formation condition of the sample immediately after the sample is collected, for example at the wellsite.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

Illustrative embodiments of the present disclosure are directed to a test method and a test apparatus that employs a microfluidic device to characterize properties of a fluid. The test method and apparatus are useful in studying the effects of different formation injection additives on the particular reservoir fluid for different flow pressures and/or additive concentrations as desired. Such operations can be used to optimize a strategy for reservoir fluid production and/or transportation that minimizes the formation of scale during these processes.

In a first aspect, a test method is described for characterizing properties of a fluid. A microfluidic device is provided having at least an inlet port, an outlet port, and a microchannel as part of a fluid path between the inlet port and the outlet port. The fluid is introduced into the microchannel and the fluid is maintained at a constant temperature in the microchannel. The fluid is evaluated while the pressure of the fluid in the microchannel is adjusted. A property of the fluid in the microchannel is characterized based on the evaluation of the fluid. The property of the fluid may relate to a scale onset pressure, which is the pressure of the fluid when scale begins to form. The adjustment of the pressure, the evaluation of the fluid, and the fluid characterization may be repeated until a scale onset formation condition occurs.

Also, in one embodiment, images of the fluid in the microchannel may be captured. The evaluation of the fluid may include an analysis of the captured images in order to determine whether such images include information that indicates the presence of scale formation in the fluid in the microchannel.

In a second aspect, a test method is described for characterizing properties of a fluid. A microfluidic device is provided having at least an inlet port, an outlet port, and a microchannel as part of a fluid path between the inlet port and the outlet port. A flow of the fluid is generated through the microchannel at a variable flow rate and a temperature of the fluid flowing through the microchannel is maintained. A pressure difference of the fluid across the microchannel and an average pressure of the fluid between an inlet and an outlet of the microchannel are measured and recorded. The pressure difference is evaluated or analyzed while the flow rate is varied to determine whether the fluid in the microchannel flowing through the microchannel exhibits characteristics indicative of the presence of scale formation.

In one embodiment, the evaluation or analysis of the pressure difference includes determining if the pressure difference varies linearly with the flow rate, wherein, if it is determined that the pressure difference varies linearly with the flow rate, then it is further determined that the fluid in the microchannel does not exhibit characteristics indicative of the presence of scale formation, and if it is determined that the pressure difference varies non-linearly with the flow rate, then it is further determined that the fluid in the microchannel does exhibit characteristics indicative of the presence of scale formation.

In one embodiment, scale onset pressure is identified as the average pressure recorded at a transition point where the pressure difference transitions between varying linearly and non-linearly with the flow rate and between varying non-linearly and linearly with the flow rate. The fluid includes at least one of a reservoir fluid, a scale inhibitor, water, and a gas.

According to a third aspect, a test apparatus is described for characterizing properties of a fluid. The apparatus includes a microfluidic device having at least an inlet port, an outlet port, and a microchannel as part of a fluid path between the inlet port and the outlet port. The apparatus also includes a temperature-controlled surface that is thermally-coupled to the microfluidic device and configured to maintain a temperature of the microchannel of the microfluidic device. Also, the apparatus includes at least one temperature sensor for measuring a temperature characteristic of the microchannel of the microfluidic device. Further the apparatus includes means for introducing the fluid into the microchannel, and a pressure sensor configured to measure pressure of the fluid in the microchannel. In addition, the apparatus includes means for adjusting the pressure of the fluid in the microchannel while the temperature characteristic is maintained for evaluation of the fluid while the pressure is adjusted to characterize properties of the fluid in the microchannel based on the evaluation of the fluid.

In one embodiment, the apparatus includes a light source and camera configured to capture images of the microchannel of the microfluidic device and fluid in the microchannel. Also, in one embodiment, the test apparatus includes means for evaluating or analyzing the images captured by the camera in order to determine whether such images include information that indicates the presence of scale formation in the fluid that flows through the microchannel of the microfluidic device at a respective adjusted pressure. The means for adjusting the fluid pressure is constructed to iteratively adjust the fluid pressure and the means for evaluating or analyzing the images is constructed to iteratively evaluate the images captured by the camera of the fluid in the microchannel corresponding to each iterative adjustment of the fluid pressure.

In a fourth aspect, a test apparatus is described for characterizing properties of a fluid. The apparatus includes a microfluidic device having at least an inlet port, an outlet port, and a microchannel as part of a fluid path between the inlet port and the outlet port. The apparatus includes means for generating a flow of the fluid through the microchannel at a variable flow rate. Also, the apparatus includes a temperature-controlled surface that is thermally-coupled to the microfluidic device and configured to maintain a temperature of the microchannel of the microfluidic device. The apparatus includes an inlet pressure sensor configured to measure an inlet pressure of the fluid at the inlet of the microchannel, and an outlet pressure sensor configured to measure an outlet pressure of the fluid at the outlet of the microchannel. Further, the apparatus includes measurement and recording means for measuring and recording a pressure difference between the inlet and outlet pressures and measuring and recording an average of the inlet and outlet pressures. In addition, the apparatus includes means for evaluating or analyzing the pressure difference while the flow rate is varied to determine whether the fluid in the microchannel flowing through the microchannel exhibits characteristics indicative of the presence of scale formation.

In one embodiment, the means for evaluating or analyzing determine if the pressure difference varies linearly with the flow rate, wherein, if it is determined that the pressure difference varies linearly with the flow rate, then it is further determined that the fluid in the microchannel does not exhibit characteristics indicative of the presence of scale formation, and if it is determined that the pressure difference varies non-linearly with the flow rate, then it is further determined that the fluid in the microchannel does exhibit characteristics indicative of the presence of scale formation. Also, in one embodiment, the means for evaluating or analyzing identify a scale onset pressure, where scale begins to form, as the average pressure recorded at a transition point where the pressure difference transitions between varying linearly and non-linearly with the flow rate and between varying non-linearly and linearly with the flow rate.

In a fifth aspect, a test method is described for characterizing properties of a fluid. A microfluidic device is provided having at least an inlet port, an outlet port, and a microchannel as part of a fluid path between the inlet port and the outlet port. The fluid is introduced into the microchannel and the fluid in the microchannel is maintained at a constant pressure. The pressure and temperature of the fluid in the microchannel are measured and recorded. Properties of the fluid in the microchannel are characterized based on evaluation of the fluid while the temperature of the fluid in the microchannel is adjusted. The properties of the fluid may relate to the scale onset temperature, which is the temperature when scale begins to form. The adjustment of the temperature, the evaluation of the fluid, and the characterization of the properties of the fluid may be repeated until the scale onset formation condition occurs.

In one embodiment, images of the fluid in the microchannel are captured. Evaluation of the fluid may include an analysis of the captured images in order to determine whether such images include information that indicates the presence of scale formation in the fluid in the microchannel.

In a sixth aspect, a test apparatus is described for characterizing properties of a fluid. The apparatus includes a microfluidic device having at least an inlet port, an outlet port, and a microchannel as part of a fluid path between the inlet port and the outlet port. The apparatus includes means for introducing the fluid into the microchannel, means for maintaining a constant pressure of the fluid in the microchannel, and a temperature-controlled surface that is thermally-coupled to the microfluidic device and configured to adjust a temperature of the microchannel of the microfluidic device. Also, the apparatus includes a pressure sensor configured to measure the pressure of fluid in the microchannel, a temperature sensor constructed to measure the temperature of fluid in the microchannel, and means for evaluating properties of the fluid while the temperature of the fluid is adjusted. In one embodiment, properties of the fluid relate to scale onset temperature.

Also, in one embodiment, the test apparatus can include a light source and camera configured to capture images of the microchannel of the microfluidic device and fluid in the microchannel. Further, the test apparatus may include means for characterizing properties of the fluid in the microchannel based on the evaluation of the fluid, the means constructed to determine, responsive to analyzing the captured images, whether the images include information that indicates the presence of scale formation in the fluid in the microchannel.

The fluid introduced into the microchannel can include at least one of a reservoir fluid, a scale inhibitor, a water-based fluid (such as seawater, freshwater, or steam), and a gas.

DETAILED DESCRIPTION

Illustrative embodiments of the present disclosure are described below. In the interest of clarity, not all features of an actual implementation are described in this specification. It will be appreciated that in the development of any such actual embodiment numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure. Further, like reference numbers and designations in the various drawings indicate like elements.

For the purposes of this disclosure, the term "reservoir fluid" means a fluid stored in or transmitted from a subsurface body of permeable rock. Thus "reservoir fluid" may include, without limitation, hydrocarbon fluids, saline fluids such as saline water, as well as other formation water, and other fluids such as carbon dioxide in a supercritical phase.

Moreover, for the purposes of this disclosure, the term "microfluidic device" means a device having a fluid-carrying channel exhibiting a width within a range of tens to hundreds of micrometers, but exhibiting a length that is many times longer than the width of the channel. Similarly the term "microchannel" means a fluid-carrying channel exhibiting a width within a range of tens to hundreds of micrometers. Although many of the microchannels described herein are of rectangular cross-section due to the practicalities of fabrication techniques, the cross-section of a microchannel can be of any shape, including round, oval, ellipsoid, square, etc.

A microfluidic device employs one or more microchannels (capillaries) where the surface area in contact with fluid flowing in the microchannel is relatively large compared to the volume of the fluid flowing through the microchannel. As a result, the heat transfer between the sample and its surroundings is rapid and the temperature of the fluid in the microchannel can be changed rapidly. Also, due to the small dimensions of the microchannel, the sample volume required in the microfluidic device amounts to a few microliters of liquid. For example, the size of a microchannel's cross-section is on the order of the length scale of reservoir pores (10 to 100 microns).

Therefore, the testing methods and apparatus described herein utilize a microfluidic device for rapid and accurate detection of scale formed in a fluid sample flowing through the microfluidic device, the temperature of which can be precisely controlled and maintained. The pressure-driven flow of the fluid sample in the microfluidic device is monitored using pressure sensors to identify properties of the scale formation condition (or the scale re-dissolution condition).

Figure 1:
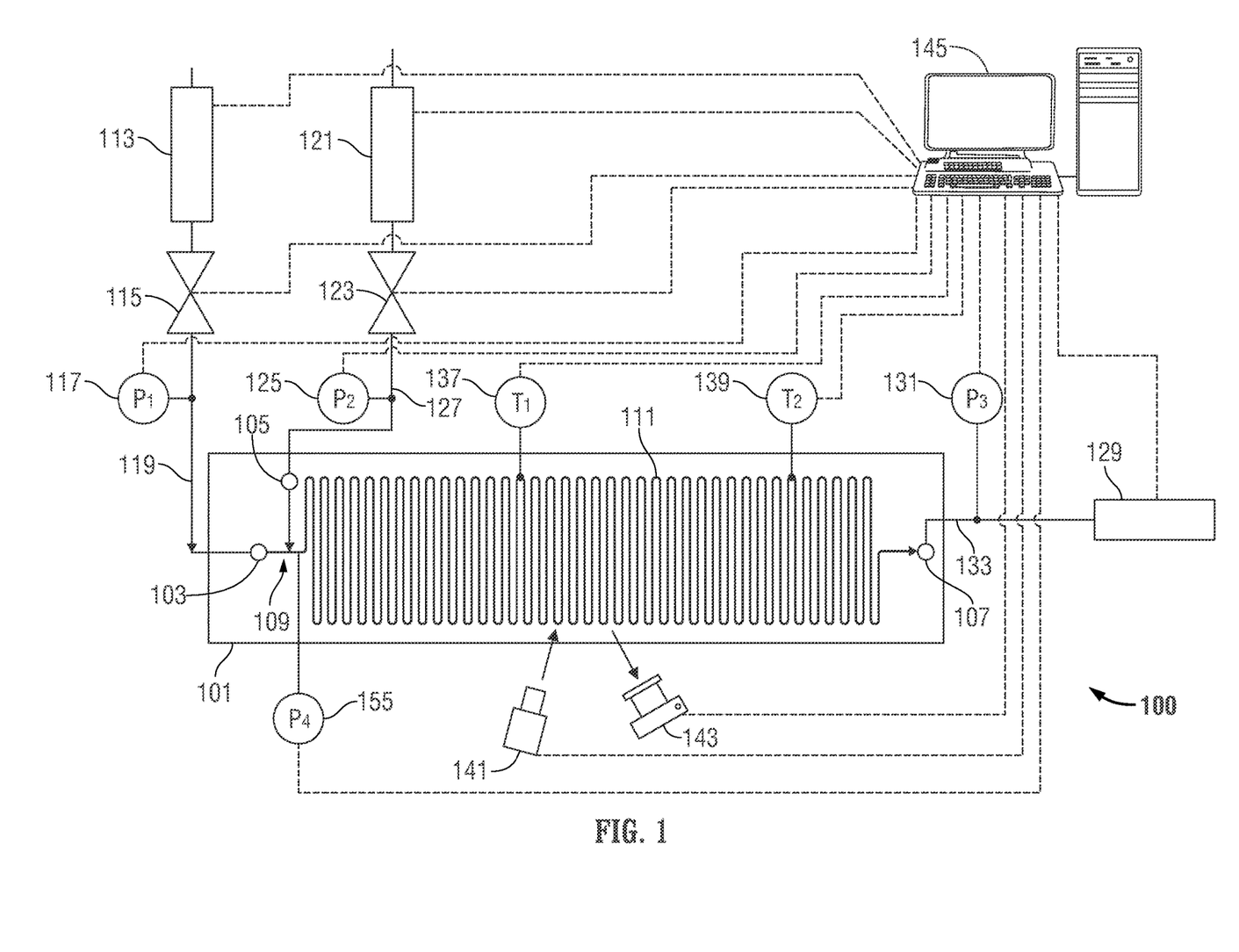
FIG. 1 is a schematic diagram of a test apparatus according to an embodiment of the present disclosure.
Figure 2:
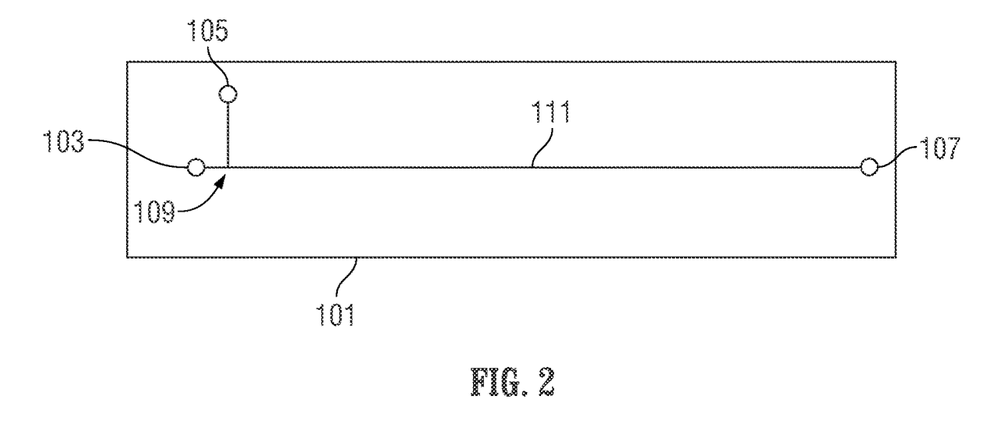
FIG. 2 is a schematic top view of another embodiment of a microfluidic device that can be used as part of the test apparatus of FIG. 1.

As shown in FIG. 1, a test apparatus 100 includes a microfluidic device 101 that includes a first inlet port 103, a second inlet port 105, and an outlet port 107. The microfluidic device 101 also includes an internal mixing section 109 (which can be a t-junction as shown) that is fluidly coupled to both the first inlet port 103 and the second inlet port 105 as well as to a microchannel 111 that extends between the mixing section 109 and the outlet port 107. The mixing section 109 can be of various forms and shapes, such as the active and passive mixers commonly used in microfluidic applications. The mixing section 109 can also be external to the microfluidic device 101. In the embodiment shown in FIG. 1, the microchannel 111 can form a serpentine pattern, thus allowing the microchannel 111 to extend a significant length but occupy a relatively small area. For example, the length of the serpentine pattern can be 1.7 meters. In another embodiment shown in FIG. 2, the microchannel 111 can extend in a linear manner between the mixing section 109 and the outlet port 107. In both the serpentine and straight microchannel configurations, the microchannel 111 has a uniform rectangular cross-section, which, in one embodiment, has a width of about 100 micrometers and a height of about 50 micrometers. However, other geometric shapes and dimensions could also be used. The microfluidic devices can be made from BOROFLOAT® glass (available from SCHOTT North America, Inc. of Louisville, Ky., USA) and silicon using standard micro-fabrication processes.

Figure 3:
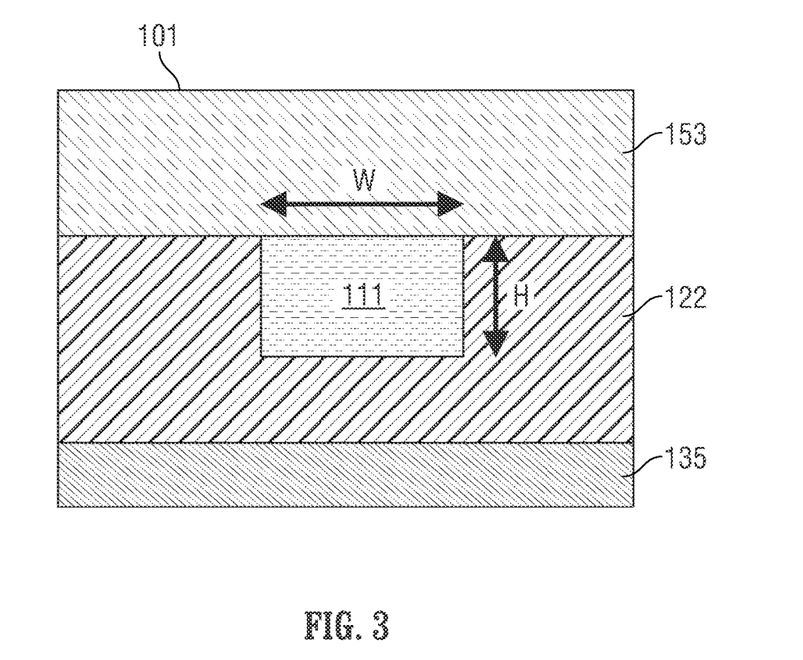
FIG. 3 is a schematic cross-sectional view of an embodiment of the microfluidic device of FIG. 1 or FIG. 2 in conjunction with a temperature-controlled heating-cooling surface that is placed in thermal contact with the microfluidic device.

In one embodiment shown in FIG. 3, the mixing section 109 and the microchannel 111 of the microfluidic device 101 can be defined by etching the planar surface of a first substrate 122. The first substrate 122 can be made of silicon (e.g., a conventional silicon-on-insulator wafer) or other suitable material. A second substrate 153 can be sealably bonded to the planar surface of the first substrate 122 that has been etched to form the mixing section 109 and the microchannel 111. The bonding can employ an anodic bonding method after careful cleaning of the bonding surfaces of the first and second substrates 122, 153. The first substrate 122 or the second substrate 153 can define the first and second inlet ports 103, 105 and the outlet port 107 that are in fluid communication with the mixing section 109 and the microchannel 111. The second substrate 153 can be made of glass, such as borosilicate glass (such as BOROFLOAT® glass) or other suitable material. The flow paths of the mixing section 109 and the microchannel 111 can have uniform rectangular cross-sections formed in the first substrate as shown in FIG. 3. In one example, such rectangular cross-sections have a width (W) of 100 μm and a height (H) of 50 μm. However, the cross-sections can have other geometric shapes as desired.

The microfluidic device 101 can be supported by (or otherwise thermally coupled to) a temperature-controlled cooling/heating surface 135 that provides for temperature control of the microfluidic device 101 (including the microchannel 111 therein) independent of the temperature of the rest of the apparatus.

Turning back to FIG. 1, the test apparatus 100 also includes an electrically-controlled reservoir and pump 113 that are loaded with a quantity of the reservoir fluid sample that contains one or more components that can precipitate out as scale. The reservoir and pump 113 have an outlet that is fluidly coupled to an electrically-controlled valve 115. The reservoir and pump 113 and the valve 115 are operated to introduce the reservoir fluid (for example, at or near a constant flow rate) into the first inlet port 103 of the microfluidic device 101. A pressure sensor 117 (such as the Sensotreme sensor available from Sensotreme GmbH of Ramsen, Switzerland) is disposed within the supply line 119 between the valve 115 and the first inlet port 103 in order to monitor the pressure of the fluid sample in the supply line 119. The reservoir and pump 113 can be an electrically-controlled syringe pump, such as the ISCO 65D pump available from Teledyne Technologies Inc. of Lincoln, Nebr., USA. The supply line 119 can include an in-line filter that removes particulate matter that could potentially clog the microchannel 111 of the microfluidic device 101. The reservoir and pump 113, the valve 115, and the supply line 119 can all operate at or near ambient temperature.

The test apparatus 100 also includes an electrically-controlled reservoir and pump 121 that are loaded with a quantity of liquid or possibly a gas. The liquid or gas can be a water-based fluid (such as produced water, flowback water, connate (formation) water, cross-linkers, gelling agents, fluid loss additives, thermal stabilizers, breakers, biocides, stabilizers, surfactants, clay controllers, scale inhibitors, fracturing polymer solutions, seawater, fresh water, steam, injection gas, brine solution as completion fluid, or fracturing fluid which may be acid-based fluids or multiphase fluids (emulsions, foams, energized)) that can be used to stimulate production of the reservoir fluid loaded into the reservoir and pump 113. The reservoir and pump 121 have an outlet that is fluidly coupled to an electrically-controlled valve 123. The reservoir and pump 121 and the valve 123 are operated to introduce the liquid or gas (for example, at or near a constant flow rate) into the second inlet port 105 of the microfluidic device 101. A pressure sensor 125 (such as a Sensotreme sensor) is disposed within the supply line 127 between the valve 123 and the second inlet port 105 in order to monitor the pressure of the test sample fluid in the supply line 127. The reservoir and pump 121 can be an electrically-controlled syringe pump, such as the ISCO 65D pump. The supply line 127 can include an in-line filter that removes particulate matter that could potentially clog the microchannel 111 of the microfluidic device 101. The reservoir and pump 121, the valve 123, and the supply line 127 can all operate at or near ambient temperature.

An optional pressure sensor 155 (such as a Sensotreme sensor) is fluidly connected between the mixing section 109 and the microchannel 111 in order to monitor the pressure of fluid entering the microchannel 111. While the fluid pressure at the inlet of the microchannel 111 can be directly obtained using pressure sensor 155, such a pressure measurement may also be obtained using a combination of pressure measurements obtained using sensors 117 and 125. For example, instead of using sensor 155 to measure the fluid pressure at the inlet of the microchannel 111, it is possible to approximate the inlet pressure using the average of the pressures obtained using sensors 117 and 125.

The outlet port 107 of the microfluidic device 101 is fluidly coupled to a collection chamber with a pump 129. The pump 129 can be controlled to apply a back pressure to the microchannel 107 to maintain a constant pressure at the inlet 109 of the microchannel 111. A pressure sensor 131 (such as a Sensotreme sensor) is disposed within an outlet line 133 between the outlet port 107 and the pump 129 in order to monitor the pressure of the fluid flowing in the outlet line 133.

Temperature sensors 137 and 139 are connected to microchannel 111. Sensor 137 is connected upstream of sensor 139. The temperature sensors 137 and 139 can be used to monitor the temperature of the microchannel 111 of the microfluidic device 101. The temperature sensors 137 and 139 can be thermocouples, such as the Omega 5TC-TT-K 40-36 thermocouple available from Omega Engineering Inc. of Laval, Quebec, Canada. The temperature-controlled cooling/heating surface 135 (FIG. 3) can be used to control the temperature of specific sections of the microchannel 111 instead of the entire microfluidic device 101. In this case, the temperature sensors 137 and 139 can be used to measure the temperature gradient along the sections of the microchannel 111 for control of the temperature gradient by cooling/heating surface 135. The temperature-controlled cooling/heating surface 135 can be a thermo-electric plate, such as a TEC model TC-36-25 RS485, available from TE Technology, Inc. of Traverse City, Mich., USA.

A light source 141 and a camera 143 can be arranged to capture high-resolution images of the microchannel 111 of the microfluidic device 101 in order to detect the presence (or absence) of scale in the microchannel 111 as described below.

The test apparatus 100 also includes a controller and/or computer processing system 145 that includes control logic that interfaces to the electrically-controlled reservoir and pumps 113 and 121 and pump 129 via wired or wireless signal paths therebetween for control of the operation of the pumps 113, 121, and 129 that interfaces to the electrically-controlled valves 115 and 123 via wired or wireless signal paths therebetween for control of the operation of the valves 115 and 123, that interfaces to the temperature-controlled cooling/heating surface 135 via wired or wireless signal paths therebetween in order to provide for temperature control of the microfluidic device 101 (or the microchannel 111 or portions thereof), that interfaces to the pressure sensors 117, 125, 131, and 155 via wired or wireless signal paths therebetween for pressure measurements and recordation of such pressure measurements during operation of the test apparatus 100, and that interfaces to the temperature sensors 137 and 139 via wired or wireless signal paths therebetween for temperature measurements and recordation of such temperature measurements during operation of the test apparatus 100. The controller and/or computer processing system 145 can also interface to the light source 141 and/or to the camera 143 via wired or wireless signal paths therebetween in order to capture high resolution images of the microchannel 111 and for recordation of such high resolution images and possibly display of such high resolution images during operation of the test apparatus 100. The control logic of the controller and/or computer processing system 145 (which can be embodied in software that is loaded from persistent memory and executed in the computing platform of the computer processing system 145) is configured to control the different parts of the test apparatus 100 to carry out a sequence of operations (workflow) that characterizes properties related to scale formation conditions (such as the scale formation temperature and pressure) of the fluid that is introduced into the microchannel 111 of the microfluidic device 101 as described below. The control logic can be configured by user input or a testing script or other suitable data structure, which is used to configure the controller or the computer processing system 145 in order to carry out control operations that are part of the workflow as described herein. For example, the user input or the testing script or other suitable data structure can specify parameters (such as pressures, flow rates, temperatures, etc.) for such control operations of the workflow.

Figure 5:
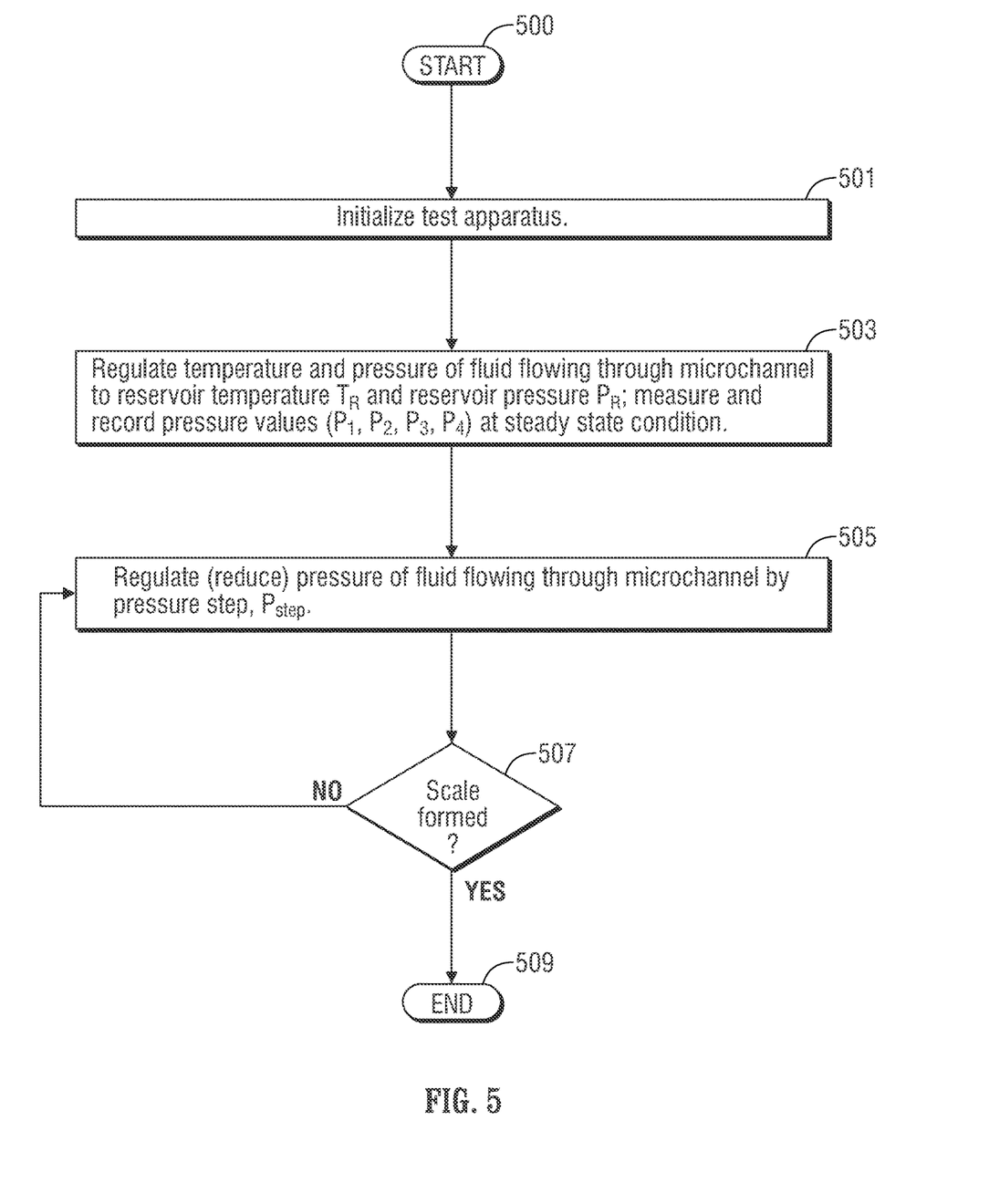
FIG. 5 is a flow chart describing a sequence of test operations carried out by the test apparatus of FIG. 1 to characterize properties related to scale onset formation conditions of fluid that flows through the microchannel of the microfluidic device.

An embodiment of a workflow is illustrated in the flow chart of FIG. 5. At 500 the workflow begins and it is assumed that the reservoir and pump 113 are filled with a sufficient quantity of the reservoir fluid sample that contains dissolved scaling chemical species and the reservoir and pump 121 are filled with a sufficient quantity of liquid or gas. The liquid or gas is a fluid to be injected into the petroleum reservoir or added to the produced fluid to test compatibility with the reservoir fluid and/or its effectiveness in preventing or reducing scale formation. For example, in a mitigation scenario, the type and relative concentration of the fluid can mimic a production environment in cases where a defined problem is arising. In a prevention scenario, prior analysis of the reservoir fluids and conditions indicate the type and formation path of potential scaling. A bespoke fluid would be prepared and its effectiveness tested, most likely in an iterative process. In some tests only the reservoir fluid sample from reservoir 113 is tested for scale onset and no liquid or gas is injected by pump 121.

At 501 the test apparatus is initialized so that reservoir and pump 113 and the corresponding valve 115 are controlled to introduce the reservoir fluid into the inlet port 103 of the microfluidic device 101 while the reservoir and pump 121 and the corresponding valve 123 are controlled to introduce the liquid or gas into the inlet port 105 of the microfluidic device 101. The pumping rates for the pumps 113 and 121 are configured such that the reservoir fluid and the liquid or gas are supplied to the inlet ports 103 and 105 at a fixed proportion. That is, the flow rates for the reservoir fluid and the liquid or gas establish the relative volume ratio of reservoir fluid to liquid or gas for the test. The flow rates, and thus the resultant relative volume ratios of reservoir fluid to liquid or gas, can be varied over multiple iterations of the test as desired.

The reservoir fluid and liquid or gas supplied to the inlet ports 103 and 105 are co-flowing fluids that flow to the mixing section 109 of the microfluidic device 101. The reservoir fluid and the liquid or gas are mixed in the mixing section 109 and can exit the mixing section 109 as a homogeneous fluid mixture. Due to the large surface-to-volume ratio of the microchannel 111, the flow of the mixture through the microchannel 111 exhibits excellent mass transfer between the co-flowing fluids. The mixture exits the microchannel 111 and flows out the outlet port 107 of the microfluidic device 101 to the collection chamber and pump 129 via the outlet line 133. The collection chamber and pump 129 is controlled to regulate a pressure of the mixture in the microchannel 111 to a pressure that varies during operations in 505 and 507.

In 503, the temperature of the fluid flow through the microchannel 111 is maintained at the reservoir temperature $T_R$. Also, the inlet pressure $P_4$ of the fluid is initially maintained at or close to reservoir pressure $P_R$ and is regulated by the collection chamber and pump 129. The reservoir pressure condition, at the reservoir temperature, is above the scale onset pressure.

The workflow carries out a sequence of operations in 505 and 507 that vary the pressure of the mixture in the microchannel 111 in order to determine properties related to the scale onset formation condition for the mixture. In each of 505 and 507, the temperature of the mixture in the microchannel 111 is controlled by maintaining the temperature of the microchannel 111 via temperature control of the temperature-controlled cooling/heating surface 135. The temperature is maintained substantially constant near the reservoir temperature, $T_R$. As mentioned earlier, temperature equilibration in the microchannel 111 can be achieved quickly due to the availability of a relatively large surface area as well as relatively small fluid volume of the microchannel 111. During the operation of 505 and 507, pressures $P_1$, $P_2$, $P_3$, and $P_4$ are measured, respectively, by the pressure sensors 117, 125, 131, and 155 and recorded by the computer processing system 145, and temperatures $T_1$ and $T_2$ are measured by the temperature sensors 137 and 139 and recorded by the computer processing system 145. Such pressures and temperatures can also be displayed on a graph relative to time for user evaluation, if desired. Such pressures and temperatures can also be stored in the memory system of the computer processing system 145 for automated data analysis if desired.

In 505, after a time period where the inlet pressure $P_4$ reaches a steady state value, and the temperatures $T_1$ and $T_2$ reach steady state values near the reservoir temperature $T_R$, the flow of the mixture stops, valves 115 and 123 are closed, and a fixed volume of the mixture is isolated in the microchannel 111. The static pressure of the mixture in the temperature-controlled section of the microchannel 111, as measured by $P_3$, is reduced in a discrete step, Pstep, by action of the collection chamber and pump 129. The pressure step, Pstep, selected may be based on an approximation based on a theoretical model of scale formation or prior testing with the test apparatus. Also, the pressure step, Pstep, can be any numerical amount that is not related to modeling or empirical testing.

Figure 4:
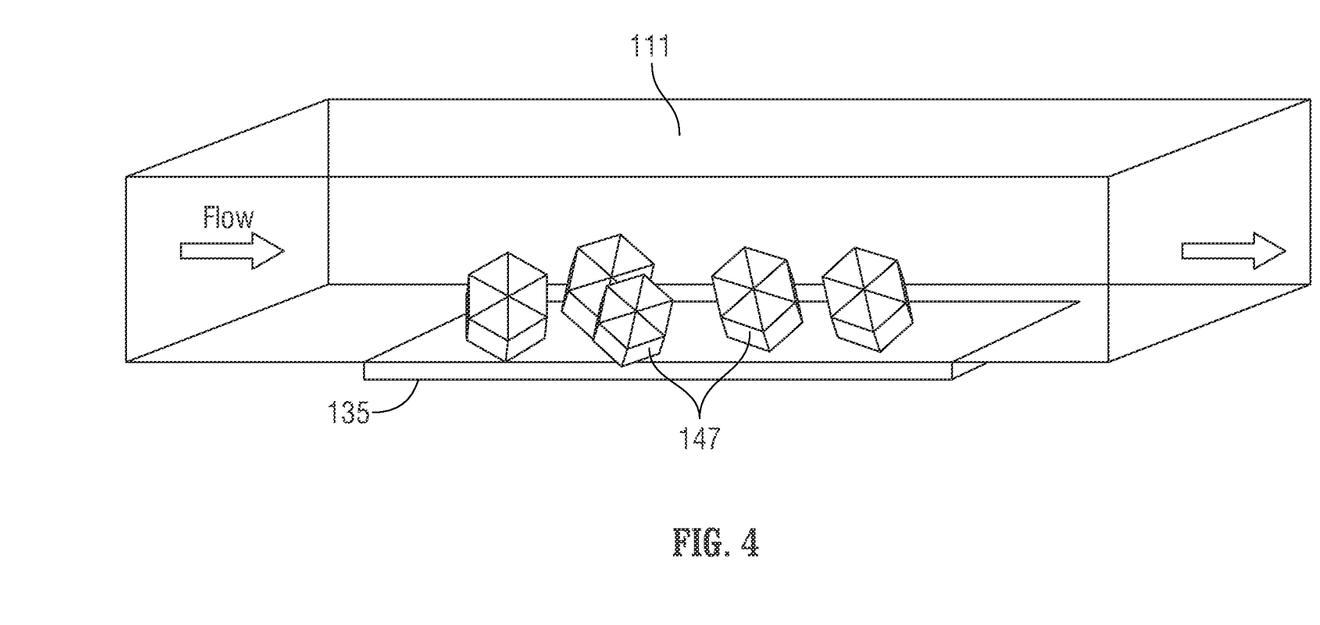
FIG. 4 is a schematic diagram showing scale deposited inside the microchannel of the microfluidic device of FIG. 1 during operation of the test apparatus.

In 507, the microchannel 111 is visually monitored with the camera 143 based on real time image analysis. FIG. 4 is a schematic representation of scale formed in the microchannel 111. The light source 141 and the camera 143 can be used to capture one or more high resolution images of the microchannel 111 as part of the evaluation of 507. Such image(s) can be displayed by the computer processing system 145 for evaluation by the operator/user to ascertain if scale is present in the image(s). Precipitates of scale will crystalize on the microchannel 111 surfaces if the reduced pressure is below the scale onset pressure. If the visual check of the microchannel 111 does not indicate scale formation (NO at 507), then the pressure is reduced again by Pstep at 505 and the microchannel 111 is checked again at 507. If the visual check of the microchannel 111 indicates that scale is formed (YES at 507), then testing ends at 509. The pressure in the microchannel 111 during the iteration of 505 and 507 when scale is indicated (YES at 507) corresponds to the scale onset pressure at the temperature in the microchannel 111, which in the example mentioned above, is at the reservoir temperature $T_R$.

Note that the evaluation of 507 can be carried out by visual interpretation of the images of the microchannel 111 by an operator/user. For fully-automated and semi-automated implementations of the workflow, such evaluation can also involve image processing of the image(s) of the microchannel 111 that is carried out by the computer processing system 145 in order to detect the presence (or absence) of scale in the microchannel 111.

The workflow shown in FIG. 5 can be repeated multiple times using different Pstep values in order to determine the scale onset pressure. It will be appreciated that larger Pstep values may reduce the number of iterations of 505 and 507 before determining the scale onset pressure, while smaller Pstep values may increase the number of iterations of 505 and 507 before determining the scale onset pressure. Moreover, it will be appreciated that larger Pstep values may yield a determination of scale onset pressure that is less accurate than if smaller Pstep values are used. Thus, there may be a tradeoff in the workflow between duration of the testing and accuracy of the result in that smaller Pstep increments may require more iterations and, thus, a longer workflow, while providing a more accurate determination of the scale onset pressure, whereas larger Pstep increments may require less iterations and, thus, a shorter workflow, while providing a less accurate (rough estimate) determination of the scale onset pressure. Also, the workflow can be repeated multiple times with different volume ratios of the reservoir fluid to the liquid or gas in order to determine the scale onset pressure of the fluid flow for the different ratios.

Figure 6:
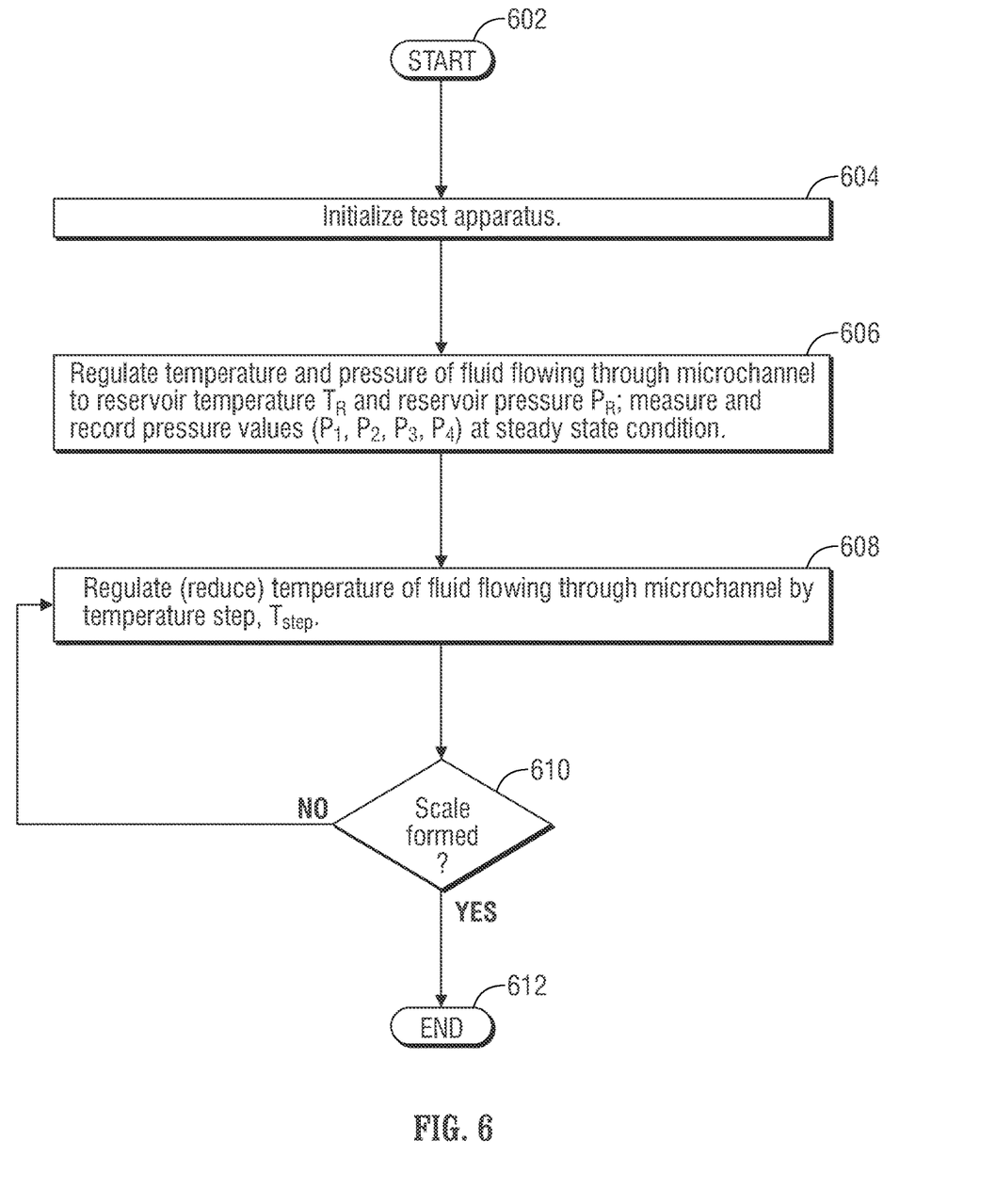
FIG. 6 is a flow chart describing a sequence of test operations carried out by the test apparatus of FIG. 1 to characterize properties related to scale onset formation conditions of fluid that flows through the microchannel of the microfluidic device.

Another embodiment of a workflow is illustrated in the flow chart of FIG. 6. At 602 the workflow begins and it is assumed that the reservoir and pump 113 are filled with a sufficient quantity of the reservoir fluid sample that contains dissolved scaling chemical species and the reservoir and pump 121 are filled with a sufficient quantity of the liquid or gas to be tested.

At 604 the test apparatus is initialized so that reservoir and pump 113 and the corresponding valve 115 are controlled to introduce the reservoir fluid into the inlet port 103 of the microfluidic device 101 while the reservoir and pump 121 and the corresponding valve 123 are controlled to introduce the liquid or gas into the inlet port 105 of the microfluidic device 101. During the operation of 604, pressures $P_1$, $P_2$, $P_3$, and $P_4$ are measured, respectively, by the pressure sensors 117, 125, 131, and 155 and recorded by the computer processing system 145, and temperatures $T_1$ and $T_2$ are measured by the temperature sensors 137 and 139 and recorded by the computer processing system 145. Such pressures and temperatures can also be displayed on a graph relative to time for user evaluation, if desired. Such pressures and temperatures can also be stored in the memory system of the computer processing system 145 for automated data analysis if desired.

The pumping rates for the pumps 113 and 121 are configured such that the reservoir fluid and the liquid or gas are supplied to the inlet ports 103 and 105 in a fixed proportion. That is, the flow rates for the reservoir fluid and the liquid or gas establish the relative volume ratio of reservoir fluid to liquid or gas for the test. The flow rates, and thus the resultant relative volume ratios of reservoir fluid to liquid or gas, can be varied over multiple iterations of the test as desired. The reservoir fluid and liquid or gas that are supplied to the inlet ports 103 and 105 are co-flowing fluids that flow to the mixing section 109 of the microfluidic device 101, which can form a homogeneous mixture. The resultant fluid mixture of the reservoir fluid and the liquid or gas flows through the microchannel 111 of the microfluidic device 101. Due to the large surface-to-volume ratio of the microchannel 111, the flow through the microchannel 111 exhibits excellent mass transfer between the co-flowing fluids. The fluid mixture exits the microchannel 111 and flows out the outlet port 107 of the microfluidic device 101 to the collection chamber and pump 129 via the outlet line 133. The collection chamber and pump 129 are controlled to regulate (such as by applying a back pressure) the pressure of the mixture in microchannel 111.

At 606, the temperature of the mixture in the microchannel is regulated to be at or close to the reservoir temperature $T_R$, while the inlet pressure $P_4$ of the mixture is regulated to be at or close to the reservoir pressure $P_R$.

A sequence of operations in 608 and 610 checks whether scale is formed at various fluid temperatures while the fluid pressure of the mixture is maintained at reservoir pressure. More specifically, the temperature of the fluid in the microchannel 111 is iteratively decreased in order to determine properties related to the scale onset formation temperature at the reservoir pressure for the fluid mixture in the microchannel 111. In each of the 608 and 610, the temperature of the bulk or mixed fluid flow in the microchannel 111 is controlled via temperature control of the temperature-controlled cooling/heating surface 135. As mentioned earlier, temperature equilibration in the microchannel 111 can be achieved quickly due to the availability of large surface area as well as small fluid volume of the microchannel 111.

In 608, after a time period where the inlet pressure $P_4$ reaches a steady state value, and the temperatures $T_1$ and $T_2$ reach steady state values near the reservoir temperature $T_R$, the flow of the mixture stops, valves 115 and 123 are closed, and a resulting fixed volume of the fluid is isolated in the microchannel 111. The pressure of the fixed volume of fluid in the microchannel 111 (as measured by any of pressure sensors 117, 125, 131, and 155 since pressure is static) is maintained by control of the collection chamber and pump 129. While the fluid pressure in microchannel 111 is maintained constant, the temperature of the fluid in microchannel 111 is decreased by a predetermined amount (Tstep) by control of the temperature-controlled cooling/heating surface 135. The temperature step, Tstep, selected may be based on an approximation informed by a theoretical model of scale formation or prior testing with the test apparatus. Also, the temperature step, Tstep, can be any numerical amount that is not related to modeling or empirical testing.

In 610, the microchannel 111 is visually monitored with the camera 143 based on real time image analysis. FIG. 4 is a schematic representation of scale formed in the microchannel 111. The light source 141 and the camera 143 can be used to capture one or more high resolution images of the microchannel 111 as part of the evaluation of 610. Such image(s) can be displayed by the computer processing system 145 for evaluation by the operator/user to ascertain if scale is present in the image(s). Precipitates of scale will crystalize on the microchannel 111 surfaces if the reduced temperature is below the scale onset temperature. If the visual check of the microchannel 111 does not indicate scale formation (NO at 610), the temperature is reduced again by Tstep at 608 and the microchannel 111 is checked again at 610. If the visual check of the microchannel 111 indicates that scale is formed (YES at 610), testing ends at 612. The temperature in microchannel 111, which can be approximated to be the average of $T_1$ and $T_2$, during the iteration of 608 and 610 when scale is indicated (YES at 610) corresponds to the scale onset temperature at the pressure in the microchannel 111, which in the example mentioned above, is at the reservoir pressure.

Note that the evaluation of 610 can be carried out by visual interpretation of the images of the microchannel 111 by an operator/user. For fully-automated and semi-automated implementations of the workflow, such evaluation can also involve image processing of the image(s) of the microchannel 111 that is carried out by the computer processing system 145 in order to detect the presence (or absence) of scale in microchannel 111.

Note that the workflow shown in FIG. 6 can be repeated multiple times using different Tstep values in order to determine the scale onset temperature. It will be appreciated that larger Tstep values may reduce the number of iterations of 608 and 610 before determining the scale onset temperature, while smaller Tstep values may increase the number of iterations of 608 and 610 before determining the scale onset temperature. Moreover, it will be appreciated that larger Tstep values may yield a determination of scale onset temperature that is less accurate than if smaller Tstep values are used. Thus, there may be a tradeoff in the workflow between duration of the testing and accuracy of the result in that smaller Tstep increments may require more iterations and, thus, a longer workflow, while providing a more accurate determination of the scale onset temperature, whereas larger Tstep increments may require fewer iterations and, thus, a shorter workflow, while providing a less accurate (rough estimate) determination of the scale onset temperature. Also, the workflow can be repeated multiple times with different volume ratios of the reservoir fluid to the liquid or gas in order to determine the scale onset temperature of the fluid flow for the different ratios.

In the workflows described with respect to FIGS. 5 and 6, the flow of the fluid mixture in the microchannel 111 is static while the respective test parameter (i.e., pressure or temperature) is iteratively changed. It will be appreciated, however, that in alternate workflows the fluid mixture introduced into the microchannel is flowing at a predetermined flow rate while the respective test parameter is iteratively changed.

Figure 7:
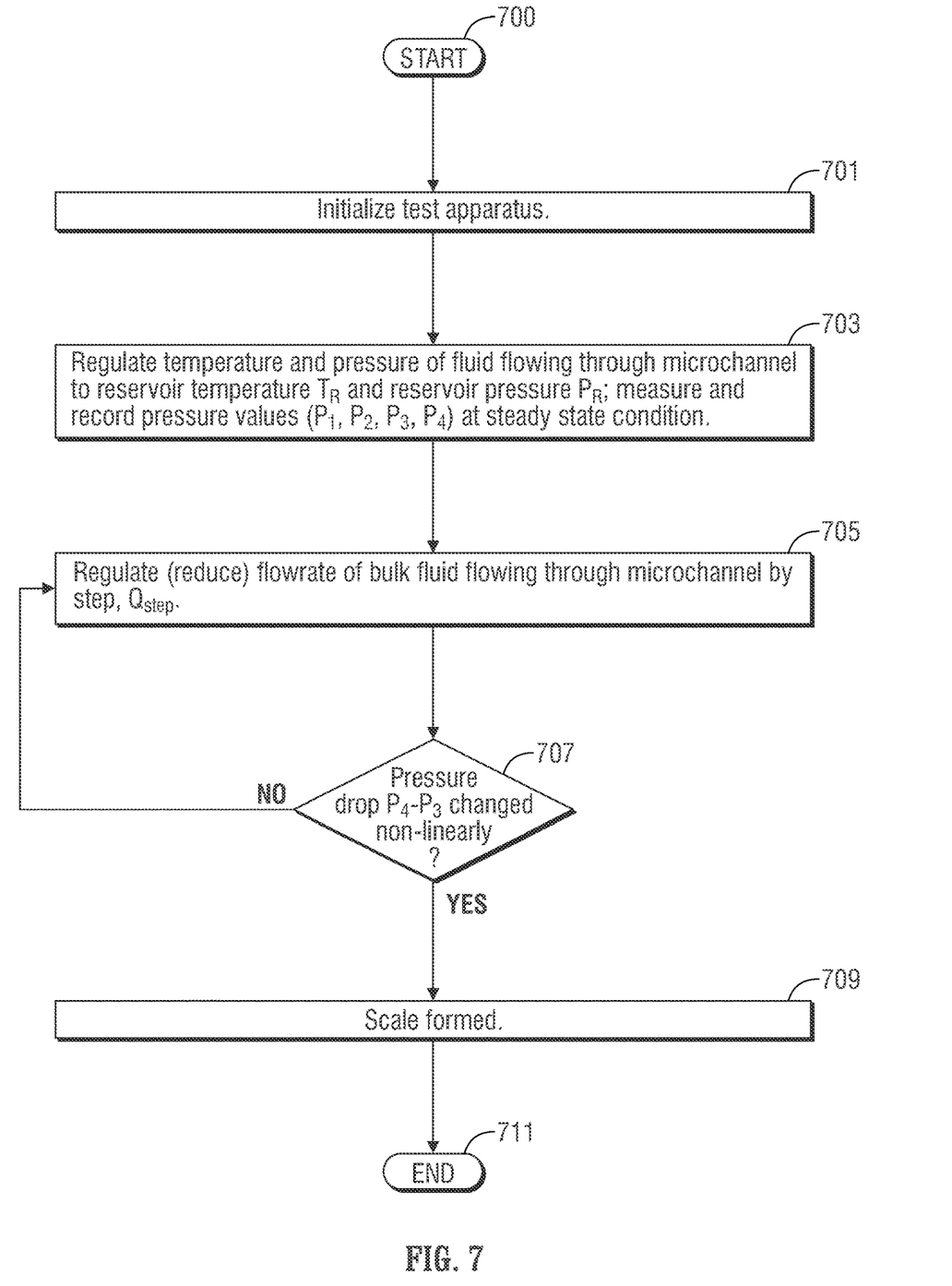
FIG. 7 is a flow chart describing another sequence of test operations carried out by the test apparatus of FIG. 1 to characterize properties related to scale onset formation conditions of fluid that flows through the microchannel of the microfluidic device.

Another embodiment of a workflow is illustrated in the flow chart of FIG. 7. The workflow begins at 700. It is assumed that the reservoir and pump 113 are filled with a sufficient quantity of reservoir fluid that contains dissolved scaling chemical species and the reservoir and pump 121 are filled with a sufficient quantity of liquid or gas to be tested. At 701 the reservoir and pump 113 and the corresponding valve 115 are controlled to introduce reservoir fluid into the inlet port 103 of the microfluidic device 101 while the reservoir and pump 121 and the corresponding valve 123 are controlled to introduce liquid or gas into the inlet port 105 of the microfluidic device 101. The pumping rates for the pumps 113 and 121 are configured such that the reservoir fluid and liquid or gas are supplied to the inlet ports 103 and 105 at constant flow rates. The flow rates for the reservoir fluid and liquid or gas establish the relative volume ratio of reservoir fluid to liquid or gas for the test. The flow rates and thus the resultant relative volume ratios of reservoir fluid to liquid or gas can be varied over multiple iterations of the test as desired. The reservoir fluid and liquid or gas that are supplied to the inlet ports 103 and 105 flow to the mixing section 109 of the microfluidic device 101, where the fluids mix to form a fluid mixture that exits mixing section 109. Due to the large surface-to-volume ratio of the microchannel 111, the mixture flowing through the microchannel 111 exhibits excellent mass transfer between the co-flowing fluids. The mixture exits the microchannel 111 and flows out the outlet port 107 of the microfluidic device 101 to the collection chamber and pump 129 via the outlet line 133.

Concurrent with the operations of 701, the workflow carries out a sequence of operations in 705 and 707 that vary the volumetric flow rate of the fluid flow through the microchannel 111 in order to determine properties related to the scale onset formation condition for the flow through the microchannel 111. In each of 705 and 707, the temperature of the mixture through the microchannel 111 is maintained at the reservoir temperature $T_R$ via temperature control of the temperature-controlled cooling/heating surface 135. As mentioned earlier, temperature equilibration in the microchannel 111 can be achieved quickly due to the availability of large surface area as well as small fluid volume of the microchannel 111. During the operation of 705 and 707, pressures $P_1$, $P_2$, $P_3$, and $P_4$ are measured by the pressure sensors 117, 125, 131, and 155 and recorded by the computer processing system 145, and temperatures $T_1$ and $T_2$ are measured by the temperature sensors 137 and 139 and recorded by the computer processing system 145. Such pressures and temperatures can also be displayed on a graph relative to time for user evaluation, if desired. Such pressures and temperatures can also be stored in the memory system of the computer processing system 145 for automated data analysis if desired.

In 703, the temperature of the mixture through the microchannel 111 is regulated such that it is maintained at the reservoir temperature $T_R$. The flow rate of the mixture is initially set high to establish a high inlet pressure $P_4$ close to reservoir pressure, where the scaling chemical species is dissolved. Thus, the high average pressure value at the reservoir temperature $T_R$ is well above the scale onset pressure for the constant flow conditions in the microchannel 111. After a time period where the inlet pressure $P_4$ reaches a steady state value near the reservoir pressure $P_R$, and the temperatures $T_1$ and $T_2$ reach steady state values near the reservoir temperature $T_R$, at 705, the flow rate of the mixture is reduced in stepwise fashion. The mixture flow rate is reduced by a step, Qstep, by reducing the respective flow rates of the reservoir fluid and the liquid or gas supplied to the inlet ports 103 and 105 at the mixing ratio set for the testing.

In a fully developed laminar flow through a circular channel, the pressure drop for driving the liquid at a specified flow rate can be calculated by using the Hagen-Poiseuille equation as follows:

$$\Delta p = \frac{128 \mu_L Q L}{\pi D_h^4} \qquad (1)$$

where $\mu_L$ is the liquid viscosity,
Q is the average volumetric flow rate through the channel,
L is the total channel length, and
$D_h$ (=4×cross-section/wetted perimeter) is the hydraulic diameter of the channel.

For a constant flow in a fixed-length channel, the pressure drop scales linearly with viscosity. However, the channel diameter can have a larger influence (fourth power of $D_h$) on the pressure drop. Therefore, a small variation in a channel cross-section or viscosity can be easily detected by monitoring the pressure drop. It should be noted that the surface-to-volume ratio varies as $D_h^{-1}$. Thus, the pressure drop required for a constant flow in the microchannel 111 is expected to be considerably higher (based on Eq. 1) when scale forms inside the microchannel 111 than in the case of simple fluid flow. The flow of the fluid carrying precipitated scale is analogous to the flow of particle suspensions, where the effective viscosity in the flow increases due to the presence of solid particles. Additionally, the deposition of scale on the internal surface of the microchannel 111 also reduces the hydraulic diameter. Both of these two effects contribute to an increase in the pressure drop in the microchannel 111 to maintain the volumetric flow.

Equation (1) can also be rewritten as follows:

$$\Delta p = KQ \quad (2)$$

where K is a flow characteristic represented by:

$$K = \frac{128 L \mu_L}{\pi D_h^4} \quad (3)$$

where $\mu_L$ is the liquid viscosity,
L is the total channel length, and
$D_h$(=4×cross-section/wetted perimeter) is the hydraulic diameter of the channel.

Thus, the inlet pressure P4 can be represented as:

$$P_4 = P_3 + KQ \quad (4)$$

When the flow characteristic K is constant, the pressure drop, and thus the inlet pressure $P_4$, vary linearly with Q. K is assumed to be constant when scale has not formed and the viscosity and hydraulic diameter are not affected by scale formation. Therefore, in the absence of scale formation occurring, the pressure drop and the inlet pressure $P_4$ are expected to vary linearly with the flow characteristic K. Specifically, if the inlet pressure $P_4$ is plotted against flow rate Q while K is constant, the inlet pressure $P_4$ would be represented by a straight line having a slope K and offset of $P_3$. However, if scale begins to form as the volumetric flow rate is changed by Qstep, then the value of the flow characteristic K would begin to deviate from the value of K before scale began to form. Such a change in the value of the flow characteristic K may be attributed to a change in viscosity of the fluid due to scale precipitate formation and/or a change in the hydraulic diameter due to scale formation on the microchannel. Thus, when scale begins to form in the flowing fluid and/or on the microchannel 111, the pressure $P_4$ would not lie on the straight line mentioned above in the case where the flow characteristic K is constant. Therefore, it is possible to denote the scale onset pressure $P_4$ by comparing an expected pressure drop (assuming a linear relationship between pressure drop and volumetric flow rate when K is constant) for each Qstep increment with the actual pressure drop measured for each Qstep increment. When the actual pressure drop measured deviates significantly from the expected pressure drop, the deviation can be attributed to scale formation and the inlet pressure $P_4$ at that formation condition can be taken to correspond to the scale onset pressure.

Specifically, the pressure difference $P_4$-$P_3$ at 707 is compared to the expected pressure difference $P_4$-$P_3$ under the steady state conditions as recorded in 703. Such comparisons provide an indication of scale formation in the microchannel 111. For example, if the pressure difference $P_4$-$P_3$ varies non-linearly with the volumetric flow rate (i.e., the pressure drop is larger than the pressure drop that would be expected after Qstep assuming no change in viscosity and hydraulic diameter), the non-linearity can be an indication that the viscosity and/or the hydraulic diameter $D_h$ has changed, which in turn can be taken to indicate that scale has formed causing the additional increase in the pressure differentials indicate higher flow resistance in the microchannel 111 caused by scale formation.

In 707, the pressure drop in microchannel 111 is compared to the expected pressure drop across the microchannel 111 based upon the flow characteristic obtained when scale is not precipitated from the mixture. If the pressure drop increased abruptly, then it is an indication that the scale onset pressure (corresponding to the reduced flow rate) has been reached (YES at 707). The magnitude of the abrupt change in pressure drop depends on the characteristics of the fluid sample, such as the amount and type of scale formed at onset, used in the test. However, in microchannels with small hydraulic diameter $D_h$, the change in pressure drop will be noticeably different after the formation of scale. If the scale onset pressure has been reached, then the inlet pressure $P_4$ at the flow rate set in 707 is recorded in the computer processing system 145 as the scale onset pressure and the workflow ends at 709. However, if the pressure drop did not increase abruptly, then it is an indication that the scale onset pressure has not been reached (NO at 707) and, therefore, the workflow proceeds back to 705 where the bulk flow rate of the mixed flow is reduced again in stepwise fashion.

Note that the evaluation of 707 can be carried out by visual interpretation of the pressure data and/or images of the microchannel 111 by the operator/user. For fully-automated and semi-automated implementations of the workflow, such evaluation can also involve signal processing of the pressure data for $P_1$, $P_2$, $P_3$, and $P_4$ that is carried out by the computer processing system 145 in order to derive an indication of scale formation and/or can involve image processing of the image(s) of the microchannel 111 that is carried out by the computer processing system 145 in order to detect the presence (or absence) of scale in the microchannel 111.

The workflow shown in FIG. 7 can be repeated multiple times using different Qstep values in order to determine the scale onset pressure. It will be appreciated that larger Qstep values may reduce the number of iterations of 705 and 707 before determining the scale onset pressure, while smaller Qstep values may increase the number of iterations of 705 and 707 before determining the scale onset pressure. Moreover, it will be appreciated that larger Qstep values may yield a determination of scale onset pressure that is less accurate than if smaller Qstep values are used. Thus, there may be a tradeoff in the workflow between duration of the testing and accuracy of the result in that smaller Qstep increments may require more iterations and, thus, a longer workflow, while providing a more accurate determination of the scale onset pressure, whereas larger Qstep increments may require less iterations and, thus, a shorter workflow, while providing a less accurate (rough estimate) determination of the scale onset pressure. Also, the workflow can be repeated multiple times with different volume ratios of the reservoir fluid and liquid or gas to be tested in order to determine the scale onset pressure of the fluid flow for the different reservoir fluid-test fluid volume ratios.

Figure 8:
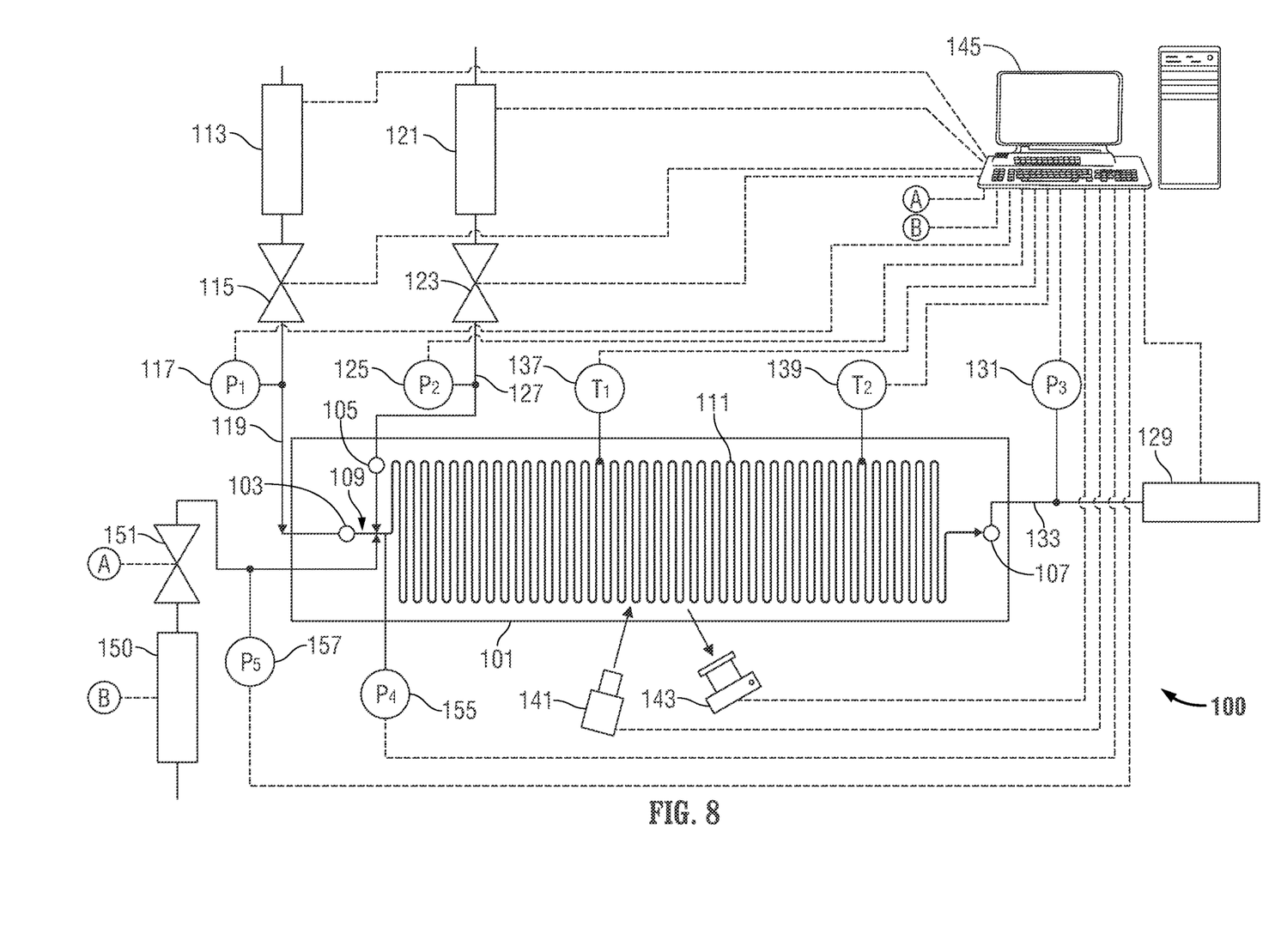
FIG. 8 is a schematic diagram of a test apparatus according to an embodiment of the present disclosure, where a fluid that includes a reservoir fluid component and possibly an additive flows through the microchannel of the microfluidic device during operation of the test apparatus. In this case, the test apparatus can be used to characterize properties related to scale onset formation conditions of the fluid that flows through the microchannel of the microfluidic device.

The test apparatus 100 (and the workflows of FIGS. 5, 6, and 7) as described herein can readily be adapted as depicted in FIG. 8 to characterize properties of scale formation for a reservoir fluid sample. FIG. 8 shows the test apparatus 100 of FIG. 1 modified with the addition of an additional reservoir and pump 150, a corresponding valve 151, and a pressure sensor 157, which are connected to the apparatus 100 between the mixing section 109 and the microchannel 111. The test apparatus 100 also includes the controller and/or computer processing system 145 that includes control logic that interfaces to the electrically-controlled reservoir and pumps 113, 121, and 150 via wired or wireless signal paths therebetween for control of the operation of the pumps 113, 121, and 150, that interfaces to the electrically-controlled valves 115, 123, and 151 via wired or wireless signal paths therebetween for control of the operation of the valves 115, 123, and 151, that interfaces to the temperature-controlled cooling/heating surface 135 via wired or wireless signal paths therebetween in order to provide for temperature control of the microfluidic device 101 (or the microchannel 111 or portions thereof), that interfaces to the pressure sensors 117, 125, 131, 155, and 157 via wired or wireless signal paths therebetween for pressure measurements and recordation of such pressure measurements during operation of the test apparatus 100, and that interfaces to the temperature sensors 137 and 139 via wired or wireless signal paths therebetween for temperature measurements and recordation of such temperature measurements during operation of the test apparatus 100. The controller and/or computer processing system 145 can also interface to the light source 141 and/or to the camera 143 via wired or wireless signal paths therebetween in order to capture high resolution images of the microchannel 111 and recordation of such high resolution images and possibly display of such high resolution images during operation of the test apparatus 100. The control logic of the controller and/or computer processing system 145 (which can be embodied in software that is loaded from persistent memory and executed in the computing platform of the computer processing system 145) is configured to control the different parts of the test apparatus 100 to carry out a sequence of operations (workflow) that characterizes properties related to scale formation condition (such as scale formation temperature and pressure) of the fluid that is introduced into the microchannel 111 of the microfluidic device 101 as described hereinabove. The control logic can be configured by user input or a testing script or other suitable data structure, which is used to configure the controller or the computer processing system 145 in order to carry out control operations that are part of the workflow as described herein. For example, the user input or the testing script or other suitable data structure can specify parameters (such as pressures, flow rates, temperatures, etc.) for such control operations of the workflow.

The remainder of the test apparatus 100 described above in connection with FIG. 1 is constructed and operates as described hereinabove and will not be repeated for the sake of brevity. The reservoir and pump 150 can optionally be filled with a sufficient quantity of an additive, such as a scale inhibitor (that inhibits formation of scale when mixed with the reservoir fluid). In this case, the reservoir and pump 113 and the corresponding valve 115 are controlled to introduce the reservoir fluid into the inlet port 103 of the microfluidic device 101, the reservoir and pump 121 and the corresponding valve 123 are optionally controlled to introduce a fluid (liquid or gas) into the inlet port 105 of the microfluidic device 101, and the reservoir and pump 150 and the corresponding valve 151 are optionally controlled to introduce the additive into the inlet port 105 of the microfluidic device 101. Thus, the construction of test apparatus 100 permits at least three fluids from the respective reservoir and pumps 113, 121, and 150 to be premixed according to a predetermined mixture ratio before entering the microchannel 111. The pumping rates for the pumps 113, 121, and 150 are configured such that the respective fluids are supplied at constant flow rates.

The workflow processes described hereinabove with respect to FIGS. 5, 6, and 7 can also be carried out using the modified test apparatus 100 shown in FIG. 8 to determine the scale onset pressure for various mixtures of reservoir fluid, fluids (such as liquid or gas), and scale inhibitors.

For example, the flow rates and, thus, the resultant relative volume ratios of reservoir fluid and scale inhibitor can be varied over multiple iterations of the test in order to study scale onset pressure for different flow pressures and/or scale inhibitor concentrations as desired. Similarly, the multiple iterations of the tests can be repeated with different scale inhibitors in order to study the effects of different scale inhibitors on the particular reservoir fluid sample at different pressures and/or scale inhibitor concentrations, as desired. The results of such test workflow operations can be used to optimize a strategy for reservoir fluid production and/or transportation that minimizes the formation of scale during these processes.

The test apparatus and the workflow as described herein may provide some advantages. The apparatus and workflow described herein can rapidly determine scale onset conditions. Also, the test apparatus and workflow are suitable for a wellsite environment. The apparatus and workflow exhibit excellent repeatability in the determination of scale onset conditions. The data obtained using the apparatus and workflow described herein is high quality data, and is comparable to conventional pressure-volume-temperature (PVT) laboratory measurements. Additionally, the apparatus and workflow described herein do not require large sample volumes and can be automated to a large extent, making them somewhat operator independent. Moreover, the apparatus and workflow described herein are suitable for testing and screening additives and scale inhibitors.

There have been described and illustrated herein several embodiments of test apparatus and method that employs a microfluidic device to characterize properties of scale formation of a fluid. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its scope as claimed.

What is claimed is:

1. A test method for characterizing properties of a fluid, comprising:
    providing a microfluidic device having at least an inlet port, an outlet port, and a microchannel as part of a fluid path between the first inlet port and the outlet port;
    introducing the fluid into the microchannel;
    maintaining a constant temperature of the fluid in the microchannel;
    adjusting the pressure of the fluid in the microchannel;
    evaluating the fluid while the pressure of the fluid is adjusted;
    characterizing a property of the fluid in the microchannel based on the evaluation of the fluid; and
    wherein the property of the fluid relates to a scale onset formation condition of the fluid at a scale onset pressure and the maintained temperature.

2. A test method according to claim 1, further comprising repeating adjusting the pressure of the fluid in the microchannel, evaluating the fluid while the pressure of the fluid is adjusted, and characterizing a property of the fluid in the microchannel based on the evaluation of the fluid until a scale onset formation condition occurs.

3. A test method according to claim 2, further comprising capturing images of the fluid in the microchannel.

4. A test method according to claim 3, wherein evaluating the fluid includes analyzing the captured images in order to determine whether such images include information that indicates the presence of scale formation in the fluid in the microchannel.

5. A test method according to claim 1, wherein the fluid introduced into the microchannel includes at least one of a reservoir fluid, a scale inhibitor, water, and a gas.

* * * * *